United States Patent [19]
Markiewitz

[11] 3,981,913
[45] Sept. 21, 1976

[54] MONO-SUBSTITUTED UREAS

[75] Inventor: Kenneth H. Markiewitz, Wilmington, Del.

[73] Assignee: ICI United States Inc., Wilmington, Del.

[22] Filed: Sept. 13, 1974

[21] Appl. No.: 505,652

Related U.S. Application Data

[62] Division of Ser. No. 372,445, June 21, 1973, which is a division of Ser. No. 880,892, Nov. 28, 1969, Pat. No. 3,763,106.

[52] U.S. Cl. .................. 260/553 R; 260/77.5 AQ
[51] Int. Cl.² ........................................ C07C 127/15
[58] Field of Search ............. 260/553 R, 77.5 AQ, 260/77.5 C, 75 NQ, 2.5 AV

[56] References Cited
UNITED STATES PATENTS

| 2,284,637 | 6/1942 | Catlin | 260/77.5 AQ |
| 3,042,631 | 7/1962 | Strandskov | 260/77.5 AQ X |
| 3,098,048 | 7/1963 | Shelanski et al. | 260/77.5 AQ |
| 3,189,653 | 6/1965 | Rudner et al. | 260/77.5 AQ X |
| 3,277,027 | 10/1966 | Hennig et al. | 260/553 R X |
| 3,321,415 | 5/1967 | Hennig et al. | 260/553 R X |
| 3,359,243 | 12/1967 | Criner | 260/77.5 SP |
| 3,663,506 | 5/1972 | Knopf et al. | 260/553 A X |
| 3,681,456 | 8/1972 | Edwards et al. | 260/77.5 AQ X |
| 3,719,639 | 3/1973 | Reetz et al. | 260/75 NQ |

*Primary Examiner*—Daniel E. Wyman
*Assistant Examiner*—Thomas A. Waltz

[57] ABSTRACT

Substituted ureas, polyurethane polymers, polyurea polymers, and polyureaurethane polymers are disclosed which are useful as textile treating agents or as intermediates for the preparation of textile treating agents. Process for treating textiles and textiles having improved durable press and abrasion resistance properties are disclosed.

11 Claims, No Drawings

MONO-SUBSTITUTED UREAS

This is a division of application Ser. No. 372,445, filed June 21, 1973, Ser. No. 372,445 is a division of application Ser. No. 880,892, filed Nov. 28, 1969, now U.S. Pat. No. 3,763,106.

This invention relates to novel compounds, to novel compositions, to methods of treating textiles, and to textiles having improved durable press and abrasion resistance properties. More particularly, this invention relates to substituted ureas, polyurethane polymers, polyurea polymers, and polyureaurethane polymers which are useful as textile treating agents or as intermediates for the preparation of textile treating agents.

During the past several years, the textile industry has become involved in the durable press treatment of textiles. Numerous textile treating agents have been proposed for imparting a durable press finish to textiles, but each of the textile treating agents proposed heretofore for imparting a durable press finish to textiles has resulted in a substantial loss of abrasion resistance to the treated textiles.

Accordingly, it is an object of this invention to provide textile treating agents which impart durable press properties to textiles treated therewith without having a substantial adverse effect on the abrasion resistance properties of the treated textiles.

It is another object of this invention to provide novel compounds which are useful as textile treating agents or as intermediates for the preparation of textile treating agents.

It is another object of this invention to provide novel compositions which are useful for treating textiles.

It is another object of this invention to provide a method for imparting durable press properties to textiles without having a substantial adverse effect on the abrasion resistance properties of the textiles.

It is another object of this invention to provide textiles having excellent durable press and abrasion resistance properties.

The novel compounds of this invention are selected from the group consisting of 1. substituted ureas characterized by the generalized formula

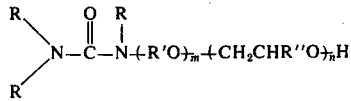

wherein $n$ is an integer from 2 to 14, $m$ is 0 or 1, R' is an alkylene group containing from 3 to 5 carbon atoms, each R'' is independently hydrogen or methyl, and each R is independently selected from the group consisting of —H and —CH$_2$OH, 2. polyurethane polymers characterized by the generalized formula

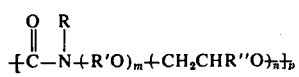

wherein $n$ is an integer from 2 to 14, $m$ is 0 or 1, $p$ is an integer from 3 to 100, R' is an alkylene group having from 3 to 5 carbon atoms, each R'' is independently hydrogen or methyl, and each R is independently selected from the group consisting of —H and —CH$_2$OH, 3. polyurea polymers characterized by the generalized formula

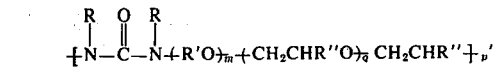

wherein $m$ is 0 or 1, $q$ is an integer from 1 to 13, $p$ is an integer from 3 to 100, R' is an alkylene group containing from 3 to 5 carbon atoms, each R'' is independently hydrogen or methyl, and each R is independently selected from the group consisting of —H and —CH$_2$OH, and 4. polyureaurethane polymers characterized by the generalized formula (A)$_x$ wherein $x$ is an integer from 2 to 100 and each A is independently selected from the group consisting of

 and

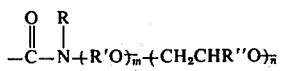

wherein $m$ is 0 or 1, $n$ is an integer from 2 to 14, $q$ is an integer from 1 to 13, R' is an alkylene group having from 3 to 5 carbon atoms, each R'' is independently hydrogen or methyl and each R is independently selected from the group consisting of —H and —CH$_2$OH, with the proviso that at least one A is

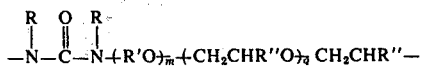

and at least one A is

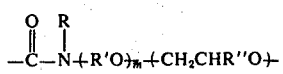

The compounds of this invention described above wherein each R is hydrogen are useful as intermediates for the preparation of textile treating agents by reacting the compounds with formaldehyde to introduce one or more methylol groups. The compounds of this invention which contain at least one methylol group are useful as textile treating agents for imparting durable press properties to textiles without having a substantial adverse effect on the abrasion resistance properties of the textiles.

The compounds of this invention wherein each R is hydrogen may be prepared by reacting urea with an aminoalcohol and/or a diamine at a temperature in the range of from about 105°C. to about 220°C. The reaction may be conducted at atmospheric pressure in a stirred resin kettle, glass flask, or other suitable equipment. The reaction may also be carried out at pressures above atmospheric pressure. The reaction may be carried out in the presence or absence of a solvent. The progress of the reaction is determined by measuring the amount of ammonia evolved. After the thermostatic amount of nitrogen is removed, the reaction product may be vacuum stripped to remove dissolved ammonia, unreacted amine, and other volitales. The methylolated products of this invention may be prepared by reacting the aforesaid reaction products with formaldehyde, paraformaldehyde or other convenient sources of formaldehyde. The reaction conditions used are those conventially used in the art for methylolating active hydrogen containing compounds.

The substituted ureas of this invention may be prepared by reacting equal molar amounts of urea and an aminoalcohol at a temperature in the range from 105° to 145°C. The reaction is unduly slow at lower temperatures, and higher temperatures result in the formation of polyurethanes. The reaction of the urea with the aminoalcohol may be carried out in the presence or absence of a solvent or a catalyst. The aminoalcohol used may be any aminoalcohol characterized by the generalized formula (a) H$_2$N$+$RO$)_m$+CH$_2$CHR''O$)_n$H wherein $m$ is 0 or 1, $n$ is an integer from 2 to 14, R is an alkylene group having from 3 to 5 carbon atoms, and each R'' is independently hydrogen or methyl. Illustrative examples of these aminoalcohols include triethyleneglycolmonoamine, tripropyleneglycolmonoamine, diethyleneglycolmonoamine, dipropyleneglycolmonoamine, pentaoxyethylenemonoamine, pentaoxypropylenemonoamine, polyoxyethylene(14)monoamine, polyoxypropylene (5)monoamine, dipropyleneglycolpropylamine, diethyleneglycolpropylamine, and decaoxyethylenepentylamine.

The polyurethane polymers of this invention may be prepared by heating a mixture of equal molar amounts of urea and aminoalcohol to a temperature from 165° to 220°C. or by heating an unmethylolated substituted urea described above to a temperature from 165° to 220°C. Temperatures above 220°C. may cause undesirable side reactions, and temperatures much below 165°C. may result in the formation of substituted ureas. The aminoalcohol used may be any of the aminoalcohols described above for the preparation of the substituted ureas.

The polyurea polymers of this invention may be prepared by reacting equalmolar amount of urea and a diamine at a temperature from about 140° to 220°C. The diamine used may be any compound characterized by the generalized formula H$_2$N $+$RO$)_m$+CH$_2$CHR''O$)_n$ CH$_2$CHR''$+$ NH$_2$ wherein $m$ is 0 or 1, $n$ is an integer from 2 to 13, R is an alkylene radical having from 3 to 5 carbon atoms and each R'' is independently hydrogen or methyl. Illustrative examples of these diamines include triethyleneglycoldiamine, hexaethyleneglycoldiamine, bis-2-aminopropyl ether of diethyleneglycol and decaethyleneglycoldiamaine.

The polyureaurethane polymers of this invention may be prepared by reacting urea with substantially equal molar amounts of a mixture of an aminoalcohol and a diamine at a temperature from 150° to 220°C. The aminoalcohol and diamine used may be any of those described above. The said mixture may contain from 10 to 90% by weight of a diamine and from 90 to 10% by weight of an aminoalcohol.

Examples 1 to 6 illustrate the preparation of substituted ureas of this invention. Additional substituted ureas may be prepared by using different aminoalcohols.

EXAMPLE 1

A stirred reaction vessel is charged with 630 grams (6 mols) of diethyleneglycolmonoamine and 360 grams (6 mols) of urea. The mixture is heated at 113° ± 7°C., and the progress of the reaction followed by weighing the amount of ammonia evolved. The reaction is stopped when 102 grams (6 mols) of ammonia is collected, about 20 hours. The reaction product is then vacuum stripped to remove any residual ammonia and other volatiles. The N-[2-(2-hydroxyethoxy)ethyl] urea product is a clear, light yellow liquid and is completely soluble in water, methanol, and ethanol. 7.4 grams of N-[2-(2-hydroxyethoxy)ethyl] urea and 12.6 ml. of 36.7% aqueous formaldehyde are added to a reaction vessel. The pH of the resulting solution is adjusted to 8.5, and the solution heated at 50°C. for 12 hours. The resulting product is an aqueous solution of the polymethylol derivative of N-[2-(2-hydroxyethoxy)ethyl] urea.

EXAMPLE 2

298 grams of triethyleneglycolmonoamine and 120 grams of urea are added to a stirred reaction vessel and heated for 25 hours at 110° to 119°C. The reaction product is vacuum stripped to remove any trapped ammonia or other volatiles. The N-(hydroxyethyldiethoxy) urea product is a clear light yellow liquid. 102 grams of this product is mixed with 24.6 grams of 36.7% aqueous formaldehyde, the pH adjusted to 8.5, and the mixture heated at 50°C. for 12 hours to form the polymethylolated product.

EXAMPLE 3

60.2 grams of pentaoxyethylenemonoamine and 12 grams of urea are mixed together in a stirred reactor and heated for 22 hours at 110°–135°C. The reaction product is then vacuum stripped to remove any residual ammonia and other volatiles. The resulting product is N-(hydroxyethyltetraethoxy) urea. The trimethylolatd derivative is prepared by reacting the said product with 49.2 grams of 36.7% aqueous formaldehyde at 50°C. for 10 hours.

EXAMPLE 4

60 grams (1 mol) urea were heated with 75 grams (1 mol) isopropanolamine at about 95°C. for three days. At that time, the correct amount of ammonia (17 grams) had been collected. The reaction product, N-[2-hydroxy, 2-methyl, ethyl] urea, after vacuum stripping is a clear deep yellow oil.

4.7 grams of N-[2-hydroxy, 2-methyl, ethyl] urea and 3.25 ml of 36.7% aqueous formaldehyde and 59 ml of water are added to a reaction vessel. The pH of the resulting solution is adjusted to 8.5 and the solution heated at 50°C. for 16 hours. The resulting product is an aqueous solution of the polymethylated derivative of N-[2-hydroxy, 2-methyl, ethyl] urea.

EXAMPLE 5

A mixture of 300 grams of aminated tetradecylethyleneglycol (3.23% nitrogen) and 39 grams of urea is heated for 3 hours at 140°C. to form

The product is a yellow, viscous oil which is soluble in water, methanol, and benzene. 7.7 grams of this product and 1.64 grams of 36.7% aqueous formaldehyde are reacted at 59°C. for 9 hours to form the methylolated product.

EXAMPLE 6

163 grams of diethyleneglycolpropylamine and 60 grams of urea are added to a 300 ml. three-necked flask and the temperature increased to reaction temperature over a one hour period. The reaction is continued for 25 hours at 108°–132°C. The reaction product is then stripped at 15–20 mm Hg absolute. The resulting diethyleneglycolpropylaminemonourea is a clear, dark yellow liquid. 4.12 grams of this product are added to 4.9 grams of 36.7% aqueous formaldehyde solution and the mixture is heated at 44°C. for 12 hours to form the methylolated derivative.

The following examples illustrate the preparation of polyurethane polymers of this invention. It is understood, of course, that additional polyurethanes may be prepared by using other aminoalcohols and substituted ureas.

EXAMPLE 7

120 grams of urea and 210 grams of diethyleneglycolmonoamine are added to a stirred reactor and heated at 130° ± 25°C. for 6 hours and then at 204° ± 10°C. for 7 hours. The resulting product is a low molecular weight polyurethane which is a yellow, viscous, oily liquid. The polyurethane contains repeating units having the formula

3 grams of the polyurethane, 5 grams of 36.7% aqueous formaldehyde, and 40 grams of water are mixed together and heated at a pH of 8.5 and 50°C. for 14 hours. The resulting methylolated polyurethane contains repeating units having the formula

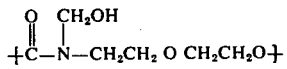

EXAMPLE 8

60 grams of urea and 163 grams of an aminoalcohol characterized by the formula

HOCH$_2$CH$_2$O CH$_2$CH$_2$ O CH$_2$CH$_2$CH$_2$NH$_2$ are reacted at 108° to 134°C. for 24 hours until the evolution of ammonia has ceased. The temperature is then raised to 180°C. for 12 hours. The resulting product, a yellow viscous oil, is a polyurethane containing repeating units having the formula

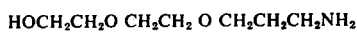

The methylolated derivative is prepared by mixing 4.12 grams of the polyurethane with 2.45 grams of 36.7% aqueous formaldehyde solution and 43.6 grams of water and heating the mixture for 14 hours at 50°C.

EXAMPLE 9

A mixture of 30 grams of urea and 330 grams of polyoxyethylene(14)monamine is heated at 119°–141°C. until evolution of ammonia has ceased, about 4½ hours. The temperature is then elevated to 178°–190°C. for 8 hours. The reaction product, a brown, viscous liquid, is a low molecular weight (below 5,000 MW) polyurethane containing repeating units having the formula

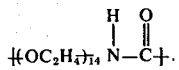

The polyurethane is then methylolated by adding 41 grams of 36.7% aqueous formaldehyde and 730 grams of water to the polyurethane and heating the resulting mixture at 50°C. and a pH of 8.5 for 14 hours.

The following examples illustrate the preparation of polyurea polymers of this invention. Additional polyurea polymers may be prepared by substituting other diamines for the diamines used in the following example.

EXAMPLE 10

90 grams (1.5 mols) of urea and 222 grams (1.5 mols) of triethyleneglycoldiamine are charged to a three-necked, round-bottom flask provided with a stirrer, thermometer, and reflux condenser vented through a dry ice trap. The reactants were heated, under an atmosphere of nitrogen, for 18 hours at 120°–165°C. The temperature was slowly raised so as to allow an orderly collection of ammonia. The reaction is terminated when the calculated amount of ammonia has formed. The product was then vacuum stripped for a short period of time to a final temperature of 185°C. The resulting polyurea polymer upon cooling is an opaque, light brown solid. A molecular weight determination using an osmometer gave a number average molecular weight of about 7,000. The polyurea polymer is soluble in water and contains 15.9% nitrogen and 0.09% amino nitrogen. A 25% solution of the polyurea polymer at 22°C. in m-cresol has a gardner-Holt viscosity of W. The polyurea polymer is then methylolated by heating a mixture of 5 grams of the polyurea polymer, 6 grams of 36.7% aqueous formaldehyde, and 69 grams of water at 51°C. for 15 hours.

EXAMPLE 11

90 grams (1.5 mols) of urea and 285 grams (1.5 mols) of dipropyleneglycoldiamine are reacted together according to the procedure of Example 10. The resulting polyurea polymer is then methylolated by heating a mixture of 6.2 grams of the polyurea polymer, 6 grams of 36.7% aqueous formaldehyde and 69 grams of water at 51°C. for 15 hours.

EXAMPLE 12

One mol of urea and one mol of tetraethyleneglycoldiamine are reacted together according to the procedure of Example 10. The resulting polyurea polymer is then methylolated by heating a mixture of 6.3 grams of the polyurea polymer, 6 grams of 36.7% aqueous formaldehyde and 69 grams of water at 51°C. for 15 hours.

EXAMPLE 13

12 grams (0.2 mols) of urea and 200 grams (0.2 mols) of polyoxypropylenediamine (polyester L1000 from Union Carbide) are charged to a three-necked, round-bottom flask provided with a stirrer, thermometer and a reflux condenser vented through a dry ice trap. The reactants are heated for 20 hours at 130°–140°C. The product is then vacuum stripped for a short period of time. The resulting polyurea polymer upon cooling is a dark amber viscous liquid. It contains 2.76% nitrogen and 0.02% amino nitrogen. The polyurea is then methylated by reacting 25 grams of the product with 25 grams of methyl formaldehyde (on 55% solution of formaldehyde in methanol), adjusting the pH to 8.5 and refluxing the solution for 3½ hours.

EXAMPLE 14

81.4 grams (0.55 mols) triethyleneglycoldiamine, 5.8 grams (0.05 mols) hexamethylene diamine and 36 grams (0.60 mols) urea are charged into a three-necked, round-bottom flask provided with stirrer, thermometer and a reflux condenser vented through a dry ice trap. The reactants are heated for 27 hours at 112°–180°C. The product is then vacuum stripped for a short period of time. The resulting polyurea upon cooling is a yellow solid. The polyurea is methylated by heating 2.5 grams of the product with 3.53 grams 36.7% aqueous formaldehyde and 32 ml of water at 50°C. overnight.

EXAMPLE 15

60.0 grams (1.0 mols) urea and 255 grams (1.0 mols) of Jeffamine D-230 (diamine having a molecular weight of 230 and available from the Jefferson Chemical Co.) are allowed to react between 112°–185°C. for 6 hours, at 185°C. for 16 hours and then terminally vacuum stripped for 6 hours up to 206°C. at 0.05 mm Hg absolute. The product is a clear, tacky solid, having a Gardner-Holt viscosity in m-cresol of S(25% solution and 25°C.). The product contains 11.1% nitrogen and has a molecular weight of 3200. This product is not water soluble.

To a solution of 215.1 grams of this product in 430.2 grams ethanol are added. 104.1 grams methyl formaldehyde (55% solution of formaldehyde in methanol, Celanese). The pH of the solution is adjusted to 8.5 and the solution is heated at 50°C. overnight. The product contains 3.0% nitrogen and is soluble in 1,1,1-trichloroethane.

The following examples illustrate the preparation of polyureaurethane polymers of this invention. Additional polyureaurethane polymers may be prepared by substituting other monoamines and diamines for those used in the illustrative examples.

EXAMPLE 16

Into a 300 ml. flask equipped with stirrer, thermometer, and receiver system, are added 37.6 grams of urea and 200 grams of a crude aminated triethylene glycol containing substantially equal molar proportions of triethyleneglycoldiamine and triethyleneglycolmonoamine. The mixture is then heated between 97°–159°C. for 3 hours, between 159°–181°C. for 1 hour, and then between 181°–190°C. for 8 hours. The reaction product is terminally vacuum stripped at 15–20 mm Hg absolute. The resulting polyureaurethane polymer is a dark, viscous liquid having a molecular weight of 1500 and a Gardner Holt viscosity in m-cresol of N(25% solution and 25°C.). To a solution of 5 grams of the polyureaurethane polymer in 63.9 grams of water are added 7.1 grams of 36.7% aqueous formaldehyde. The pH of the solution is adjusted to 8.5, and the solution is heated at 51°C. for 15 hours.

EXAMPLE 17

A mixture of 74 grams (0.5 mol) of triethyleneglycoldiamine, 74 grams (0.5 mol) of triethyleneglycolmoneamine, and 60 grams (1 mol) of urea is heated at 84°–130°C. for 22 hours and then at 150°–180°C. for 51 hours. 2.5 grams of the resulting polyureaurethane polymer is added to 3.6 grams of 36.7% aqueous formaldehyde solution and 32 grams of water. The resulting solution is then heated at 50°C. for 12 hours.

EXAMPLE 18

39 grams of urea and 300 grams of an equal molar mixture of tetradecylethyleneglycoldiamine and tetradecylethyleneglycolmonoamine are heated at 119°–141°C. for 4½ hours. The temperature is then raised to 178°–190°C. for 8 hours. The resulting polyurethane polymer is a brown viscous liquid. The polyureaurethane polymer is then methylolated by heating a mixture of 5 grams of the polymer, 0.85 gram of a 36.7% aqueous formaldehyde, and 47.2 grams of water for 15 hours at 50°C.

EXAMPLE 19

74.5 grams (1.24 mols) of urea, 142.9 grams (0.62 mols) of Jeffamine D-230 (bis-2-aminopropyl ether of diethylene glycol) and 65.3 grams (0.62 mols) diethyleneglycolmonoamine are charged to a three-necked, round-bottom flask provided with stirrer, thermometer and reflux condenser vented through a dry ice trap. The mixture was then heated for 6 hours between 104°–175°C., 16 hours at 175°C., 4 hours at 195°C. and then terminally vacuum stripped for 2 hours at 195°C. at 15–20 mm Hg absolute. The product was a yellow oil containing 11.2% nitrogen.

To a solution of 212 grams of this product in 424 grams of water are added 172 ml of 37% aqueous formaldehyde. The pH of the solution is adjusted to 8.5 and the solution allowed to react at room temperature overnight. The product is a clear yellow solution which becomes turbid above 30°C.

In accordance with the present invention, the above described compounds which contain at least one methylol group may be applied to textile materials to impart durable press properties thereto without having a substantial adverse effect on the abrasion resistance of the treated textiles. It has been found that if textile material which has been treated with the methylolated compounds of the present invention is cured at an elevated temperature, the methylolated compounds are attached to the textile material so that the durable press and abrasion resistance properties imparted to the textile material are not removed by subsequent washing or drycleaning.

The methylolated compounds of this invention may be applied to the textile material alone or in combination with hand modifiers and/or cellulose-reactive cross-linking crease-proofing agents known in the art for treating textile materials. The methylolated compounds of this invention, hand modifiers, and crease-proofing agents may be combined to produce novel textile treating compositions of the present invention in the following proportions of percentage composition by weight (based on the total weight of named ingredients):

TEXTILE TREATING COMPOSITION A

|  | Broad Range | Preferred Range |
|---|---|---|
| Methylolated compound of the invention | 99–70% | 95–85% |
| Hand Modified | 1–30% | 5–15% |

TEXTILE TREATING COMPOSITION B

|  | Broad Range | Preferred Range |
|---|---|---|
| Methylolated compound of this invention | 20–80% | 40–60% |
| Crease-proofing agent | 80–20% | 60–40% |

TEXTILE TREATING COMPOSITION C

|  | Broad Range | Preferred Range |
|---|---|---|
| Methylolated Compound of this invention | 20–80% | 40–60% |
| Crease-proofing agent | 80–20% | 60–40% |
| Hand Modifier | 1–20% | 5–15% |

Illustrative examples of modifiers or softeners which may be employed with the methylolated compounds of this invention include polyethylene emulsions such as MYKON SF and Poly-Em No. 20017, methylolated oleamide, polyacrylamide, polyethyleneglycol, polyvinylalcohol, and methylolmonoamides.

Typical examples of cellulose-reactive cross-linking crease-proofing agent with which the methylolated compounds of this invention may be used satisfactorily include dihydroxy dimethylol ethylene urea; 1,3-dimethylol-4,5-dihydroxyimidazolidone-2; 1,3-dimethylolimidazolidone-2; dimethylol propylene urea; dimethylol-5-hydroxy propylene urea; dimethylol-5-methyl propylene urea; dimethylol-5,5-dimethyl propylene urea; dimethylol-4-methoxy-5,5-dimethyl propylene urea; dimethylol triazone; bis(methoxymethyl) uron; dimethylol methyl carbamate; monomethylol ethyl carbamate; dimethylol methoxy ethyl carbamate; melamine-formaldehyde reaction product; guanamine and substituted guanamine reaction products; urea-formaldehyde reaction products; aldehydes such as formaldehyde and glyoxal; aldehyde derivatives such as tetramethylolacetone and diethyleneglycolacetal; epoxides such as ethylene glycol diglycidyl ether and vinylcyclohexene dioxide; and ethyleneimine derivatives such as bisaziridinylcarbonyl and tris(1-aziridinyl) phosphine oxide.

This invention is not restricted to the aforementioned hand modifiers and crease-proofing agents. The methylolated compounds of the present invention do not affect the hand modifiers and crease-proofing agents as such, but brings about modification of the properties of the textile itself. Consequently, it is an obvious advantage of this invention that the said methylolated compounds can be used in conjunction with all types of hand modifiers and crease-proofing agents known in the art.

The methylolated compounds of this invention and mixtures thereof with hand modifiers and/or crease-proofing agents may be applied to textile materials from an aqueous medium, an organic solvent, or an emulsion of water and organic solvent. Illustrative examples of organic solvents which may be used include isopropanol, 1,1,1-trichloroethane, 1,1,2-trichloroethane, perchloroethylene, carbon tetrachloride, chloroform, pentachloroethane, and dichlorobenzene. Illustrative examples of surfactants which may be used to emulsify the textile treating compositions of this invention in organic solvents include polyoxyethylene(25) caster oil, isopropylamine dodecylbenzene sulfonate, diethyl sulfate quaternary of polyoxyethylene(20)hydrogenated tallow amine, and polyoxyethylene(10)nonyl phenol.

Textile material may be treated with a bath containing a methylolated compound of this invention by any suitable means, such as by immersion therein or by spraying. In the immersion method of application, the textile material may either be run through a padding machine wherein the textile material is first dipped into the bath and then squeezed, or the textile materials may be dipped into the bath and the excess liquid extracted by centrifugation. In the spraying method of application, the textile materials are simply sprayed with a bath containing the methylolated compound and then dried by any suitable means.

The amount of methylolated compound of this invention which is applied to the textile material may vary over a wide range and will depend, mainly, on the degree of durable press properties desired. In general, the methylolated compounds are applied to textiles in amounts with the range of about 1% to about 20%, and preferably from about 5% to about 15% based on the dry weight of the textile.

Textile material which has been treated with the methylolated compounds of this invention may be cured by heating the treated textile material in the presence of an acid catalyst. The acid catalyst and methylolated compound may be applied to the textile material simultaneously or in separate steps as is conventional in the art. Illustrative examples of curing catalyst include zinc nitrate, ammonium chloride, ammonium dihydrogen phosphate, ammonium thiocyanate, aluminum sulfate, magnesium sulfate, magnesium chloride, triethanolamine hydrochloride, and triethylamine hydrochloride. The amount of acid catalyst used is the amount conventionally used in the art for curing methylolated durable press agents onto textile material. In general, satisfactory results are obtained by using from 6 to 36% of catalyst based on the weight of methylolated compound used. The heat cure of the textile material treated with catalyst and methylolated compound may be effective at temperatures from about 300° to 350°F. in periods of time ranging from about 10 to about 15 minutes at the lower temperature to about 2 to 3 minutes at the higher temperature. The reaction may take place at lower temperature if the curing time is extended. Higher temperatures may also be employed.

The textile materials which may be treated with the methylolated compounds of this invention include textiles composed of cellulose or modified cellulose, such as cotton, rayon, linen, etc., and mixtures thereof, either with each other or with non-cellulosics such as nylon, polyesters such as Dacron (polyethylene terephthalate), Acrilan (an acrylic fiber containing 85% polymerized acrylonitrile and 15% vinyl acetate), wool, etc. The textile material may be in the form of filaments, fibers, yarns, threads, etc., or in woven, nonwoven, knit or otherwise formed fabrics, sheets, and cloths.

EXAMPLE 20

To a solution of 60 grams of the unmethylolated polyurea polymer of Example 10 in 327.5 grams of water are added 42.5 grams of 36.7% aqueous formaldehyde. The pH of the solution is adjusted to 9 and the solution heated for 15 hours at 50°C. 13.5 grams of zinc nitrate hexahydrate are added and the solution diluted to 740 grams with water. The pH is adjusted to 5. The solution contains 10.2% methylolated polyurea polymer and 1.5% zinc nitrate hexahydrate. The solution is applied to poplin cloth to give a wet pickup of 80%. The cloth is then dried at 100°C. for 5 minutes and cured at 160°C. for 10 minutes. The properties of the cloth are described in Table I.

EXAMPLE 21

To a solution of 2.5 grams of the unmethylolated polyurea polymer of Example 10 in 34.5 grams of water are added 3.5 grams of 36.7% aqueous formaldehyde. The pH of the solution is adjusted to 8.5 and the solution heated for 15 hours at 50°C. 1.3 grams of MYKON SF polyethylene emulsion and 0.57 grams of zinc nitrate hexahydrate are added to the solution. The pH is adjusted to 5.7 and the solution diluted to 42.2 grams with water. The solution contains 9% methylolated polyurea polymer, 3% MYKON SF, and 1.35% catalyst. Poplin cloth is treated with the solution, and cured as in Example 20. The properties of the cloth are described in Table I.

EXAMPLE 22

0.72 gram of zinc nitrate hexahydrate, 1.6 grams of MYKON SF polyethylene emulsion, and 2.58 grams of water are added to the methylolated polyurethane polymer reaction product of Example 7. The pH of the resulting solution is adjusted to 4.8. A cotton poplin swatch is padded to 80% pick-up with the solution, dried for 3 minutes at 92.5%°C. and cured for 15 minutes at 145°C. The properties of the cloth are described in Table I.

EXAMPLE 23

The methylolated substituted urea product of Example 1 is diluted with 108 ml. of water to 10% solids by weight. 1.2 grams of zinc nitrate hexahydrate are added and the solution is applied to a swatch cotton print cloth at 100% pick-up. The cloth is dried for 3 minutes at 92.5% and then cured at 160°C. for 4 minutes. The properties of the treated cloth are described in Table I.

EXAMPLE 24

The methylolated substituted urea product of Example 2 is diluted with water to 10% solids and 120 grams removed. 1.8 grams of magnesium chloride are added to the solution removed. Cotton print cloth is treated with the solution at 100% pick-up. The cloth is then heated at 92.5°C. for 3 minutes and at 160°C. for 4 minutes. The properties of the treated cloth are described in Table I.

EXAMPLE 25

The methylolated substituted urea reaction product of Example 5 is diluted to 83 grams with water and 0.83 grams of zinc nitrate hexahydrate are added. Cotton cloth is padded at 100% pick-up with the solution, and the cloth is heated at 92°C. for 3 minutes and at 160°C. for 4 minutes. The properties of the treated cloth are described in Table I.

EXAMPLE 26

4.12 grams of the unmethylolated substituted urea reaction product of Example 6 and 4.9 grams of 36.7% aqueous formaldehyde solution are reacted at 44°C. for 12 hours. The reaction product is diluted to 59 grams with water and 0.59 grams of zinc nitrate hexahydrate are added. This textile treating solution is then used to pad a poplin swatch at 80% pick-up. The cloth is heated at 92°C. for 5 minutes and at 160°C. for 10 minutes. The properties of the treated cloth are described in Table I.

EXAMPLE 27

The methylolated substituted urea reaction product of Example 3 is diluted with water to 10% solids and 120 grams of solution removed. 2.4 grams of dibasic magnesium phosphate are added to the solution. Cotton cloth is padded to 100% of its dry weight with the solution. The cloth is dried for 3 minutes at 92.5°C. and cured at 160°C. for 4 minutes. The properties of the treated cloth are described in Table I.

EXAMPLE 28

4.72 grams of the substituted urea reaction product of Example 4, 3.25 ml 36.7% aqueous formaldehyde and 51 ml water are reacted for several days at room temperature, holding the pH of the solution at 7.5. 590 mg of zinc nitrate hexahydrate are then added. This textile treating solution is then used to pad a cotton print cloth swatch at 80% pick-up. The cloth is heated at 92°C. for 5 minutes and at 160°C. for 4 minutes. The properties of the treated cloth are described in Table I.

EXAMPLE 29

To the methylolated polyurethane polymer product of Example 8 are added 7.44 grams of a 45% aqueous solution of dihydroxy dimethylol ethylene urea, 1.26 grams of zinc nitrate hexahydrate, and 28.7 grams of water. The pH of the solution is adjusted to 4.8 and 2.7 grams of MYKON polyethylene emulsion added. The solution contains 9% of a mixture of 60 parts methylolated polyurethane polymer and 40 parts of a 45% aqueous solution of dihydroxy dimethylol ethylene urea. Poplin cotton cloth is padded with this solution at 80% pick-up and heated at 92.5°C. for 3 minutes and 145°C. for 15 minutes. The properties of the treated cloth are described in Table I.

EXAMPLE 30

To the solution of methylolated polyureaurethane polymer prepared in Example 18 are added 7.87 grams of a 45% aqueous solution of dihydroxy dimethylol ethylene urea, 1.33 grams of zinc nitrate hexahydrate and 33 grams of water. The pH is adjusted to 4.8 and 2.95 grams of MYKON SF polyethylene emulsion are added. The solution contains 9% of a mixture of 60 parts of polyureaurethane and a 45% aqueous solution of dihydroxy dimethylol ethylene urea. Poplin cloth is treated with this solution at 80% pick-up and heated at 92.5°C. for 3 minutes and 145°C. for 15 minutes. The properties of the treated cloth are described in Table I.

EXAMPLE 31

To the solution of methylolated polyureaurethane polymer prepared in Example 16 are added 11.25 grams of a 45% aqueous solution of dihydroxy dimethylol ethylene urea, 1.9 grams of zinc nitrate hexahydrate and 4.23 grams of MYKON SF. The solution diluted to 141 grams with water and the pH adjusted to 5.7. The solution contains 5.4% methylolated polyureaurethane polymer and 3.5% of a 45% aqueous solution of dihydroxy dimethylol ethylene urea. Poplin cloth is padded, dried and cured as in Example 30. The properties of the treated cloth are described in Table I.

EXAMPLE 32

5.63 grams of a 45% aqueous solution of dihydroxy dimethylol ethylene urea, 0.95 grams of zinc nitrate hexahydrate, 2.11 grams of polyethylene emulsion, and 23.6 grams of water are added to the methylolated polyureaurethane product of Example 17 to make a textile treating solution. Cotton cloth was padded therewith at 80% pick-up and heated at 92.5°C. for 5 minutes and at 165°C. for 10 minutes. The properties of the treated cloth are described in Table I.

EXAMPLE 33

To a solution of 2.5 grams of the unmethylolated polyurea polymer of Example 10 in 34.5 grams of water are added 3.5 grams of 36.7% aqueous formaldehyde. The pH is adjusted to 8.5 and the solution heated to 50°C. for 15 hours. 5.6 grams of a 45% aqueous solution of dihydroxy dimethylol ethylene urea and 0.95 grams of zinc nitrate are added and the solution diluted to 70.25 grams with water. The solution contains 5.4% methylolated polyurea polymer, 3.6% of durable press resin and 1.35% catalyst. Poplin cloth is padded with this solution to give a wet pick-up of 80%. The cloth is heated at 100°C. for 5 minutes and at 160°C. for 10 minutes. The properties of the treated cloth are described in Table I.

EXAMPLE 34

To a solution of 3.3 grams of the unmethylolated polyurea polymer of Example 10 in 42.1 grams of water are added 4.6 grams of 36.7% aqueous formaldehyde. The pH is adjusted to 8.5 and the solution heated to 50°C. for 15 hours. To the reaction mixture are added 1.96 grams of a 45% aqueous solution of dihydroxy dimethylol ethylene urea, 2.0 grams of MYKON SF polyethylene emulsion, and 0.89 grams of zinc nitrate hexahydrate. The resulting solution is then diluted with water to a total of 65.4 grams and the pH adjusted to 5.7. The solution contains 7.65% methylolated polyurea polymer. Poplin cloth is then treated with the solution as in Example 33. The properties of the treated cloth are described in Table I.

EXAMPLE 35

5.0 grams of the polyurethane prepared in Example 7, 5.73 ml of 36.7% aqueous formaldehyde and 60 ml of water are heated at 50°C. overnight after prior adjustment of the pH to 8.5. 710 mg. of zinc nitrate hexahydrate are then added. This textile treating solution is then used to pad a cotton print cloth swatch at 80% pick-up. The cloth is heated at 92°C. for 3 minutes and at 160°C. for 4 minutes. The properties of the treated cloth are described in Table I.

EXAMPLE 36

The methylolated polyurea reaction product of Example 13 is diluted to 83 grams with methanol. 15 grams of this solution are further diluted with 45 grams methanol and 5 grams of water. After adjustment of the pH to 5.7, 0.5 grams of zinc nitrate hexahydrate are added. This textile treating solution is then used to pad a poplin swatch at 80% pick-up. The cloth is heated at 92°C. for 5 minutes and at 160°C. for 10 minutes. The properties of the treated cloth are described in Table I.

EXAMPLE 37

The methylolated polyurea reaction product of Example 14 is diluted to 63.6 grams with water, and 5.63 grams of a 45% aqueous solution of dihydroxy dimethylol ethylene urea and 0.95 grams zinc nitrate hexahydrate are added. The pH of this solution is adjusted to 5.7. This textile treating solution is then used to pad a poplin swatch at 80% pick-up. The cloth is heated at 92°C. for 5 minutes and at 165°C. for 10 minutes. The properties of the treated cloth are described in Table I.

TABLE I

| Example Number | Monsanto Crease Angle Recovery Warp Plus Fill | | Stoll Flex Abrasion Resistance Warp | | One-Inch Cut Strip Tensile Strength (lb.) Warp | Elmendorf Strength (lb.) Warp |
|---|---|---|---|---|---|---|
| | 0 Wash | 10 Washes | 0 Wash | 10 Washes | 0 Wash | 0 Wash |
| 20 | 232 | 199 | 559 | 384 | 58.3 | 0.96 |
| 21 | 287 | 266 | 1,181 | 856 | 50.6 | |
| 22 | 143[1] | | 603 | | | |
| 23 | 303 | | | | | |
| 24 | 295 | | | | | |
| 25 | 262 | | | | | |
| 26 | 235 | | | | | |
| 27 | 295 | | | | | |
| 28 | 214 | | | | | |
| 29 | 149.5[1] | 151[1] | 491 | | 57.4 | |
| 30 | 147[1] | | 680 | | | |
| 31 | 296 | 293 | 326 | | 56.5 | |
| 32 | 149[1] | 146[1] | 421 | | 57.9 | |
| 33 | 295 | 273 | 334 | 245 | 51.4 | |
| 34 | 302 | 294 | 550 | 382 | 55.0 | 1.76 |
| 35 | 243 | | | | | |
| 36 | 239 | | 513 | | | |
| 37 | 284 | 272[2] | 259 | | 53.2 | |

[1]Warp only
[2]After 5 washes.

Although this invention has been described with reference to specific materials, including specific aminoalcohols, diamines, substituted ureas, polyurethane polymers, polyurea polymers, polyureaurethane polymers, methylolating agents, durable press agents, softeners, and catalysts, it will be readily apparent that still other different and equivalent materials may be substituted for those described, all within the spirit and scope of this invention.

Having described the invention, what is desired to be secured by Letters Patent is:

1. A substituted urea characterized by the generalized formula

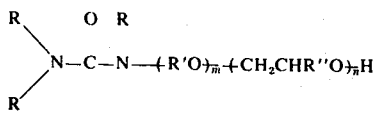

wherein $n$ is an integer from 2 to 14, $m$ is 0 or 1, R' is an alkylene group containing from 3 to 5 carbon atoms, each R'' is independently hydrogen or methyl, and each R is independently selected from the group consisting of —H and —CH$_2$OH.

2. A substituted urea of claim 1 which contains at least 1 —CH$_2$OH group.

3. A substituted urea of claim 2 wherein $m$ is 0, $n$ is 2 and R'' is hydrogen.

4. A substituted urea of claim 2 wherein $m$ is 0, $n$ is 3 and R'' is hydrogen.

5. A substituted urea of claim 2 wherein $m$ is 0, $n$ is 5 and R'' is hydrogen.

6. A substituted urea of claim 2 wherein $m$ is 0, $n$ is 14 and R'' is hydrogen.

7. A substituted urea of claim 1 wherein each R is hydrogen.

8. A substituted urea of claim 7 wherein $m$ is 0, $n$ is 2 and R'' is hydrogen.

9. A substituted urea of claim 7 wherein $m$ is 0, $n$ is 3 and R'' is hydrogen.

10. A substituted urea of claim 7 wherein $m$ is 0, $n$ is 5 and R'' is hydrogen.

11. A substituted urea of claim 7 wherein $m$ is 0, $n$ is 14 and R'' is hydrogen.

* * * * *

UNITED STATES PATENT AND TRADEMARK OFFICE
CERTIFICATE OF CORRECTION

PATENT NO. : 3,981,913
DATED : September 21, 1976
INVENTOR(S) : Kenneth H. Markiewitz It is certified that error appears in the above-identified patent and that said Letters Patent are hereby corrected as shown below:

Column 3, line 47, delete final ")" from the formula "$H_2N(RO)_m(CH_2CHR"O)_nCH_2CHR")NH_2$.

Column 6, line 4, "polyoxyethylene(14)monamine" should read -- polyoxyethylene(14)monoamine --.

Column 7, line 4, "polyester L1000" should read -- polyether L1000 --.

Column 8, line 10, "triethyleneglycolmoneamine" should read -- triethyleneglycolmonoamine --.

Column 9, line 9, "Hand Modified" should read -- Hand Modifier --.

Column 10, line 5, "caster oil" should read -- castor oil --.

Column 15, line 10, $$\begin{array}{c} R \quad O \quad R \\ \backslash \quad \quad | \\ N-C-N(R'O)_m(CH_2CHR"O)_nH \\ / \\ R \end{array}$$ should read $$\begin{array}{c} R \quad O \quad R \\ \backslash \quad \| \quad | \\ N-C-N(R'O)_m(CH_2CHR"O)_nH \\ / \\ R \end{array}$$ --.

*Signed and Sealed this*

*Fourth* Day of *October 1977*

[SEAL]

Attest:

RUTH C. MASON
*Attesting Officer*

LUTRELLE F. PARKER
*Acting Commissioner of Patents and Trademarks*